United States Patent [19]
Dreesman et al.

[11] Patent Number: 4,778,784
[45] Date of Patent: Oct. 18, 1988

[54] CYCLIC PEPTIDE AND METHOD OF USE FOR INDUCING AN IMMUNOLOGICAL RESPONSE TO HEPATITIS B VIRUS

[75] Inventors: Gordon R. Dreesman; James T. Sparrow, both of Houston, Tex.; Darrell L. Peterson, Chesterfield, Va.; Frederick B. Hollinger; Joseph L. Melnick, both of Houston, Tex.

[73] Assignee: Baylor College of Medicine, Houston, Tex.

[21] Appl. No.: 124,419

[22] Filed: Nov. 23, 1987

Related U.S. Application Data

[63] Continuation of Ser. No. 1,120, Jan. 7, 1987, abandoned, which is a continuation of Ser. No. 760,377, Jul. 30, 1985, abandoned, which is a continuation of Ser. No. 447,722, Dec. 6, 1982, abandoned.

[51] Int. Cl.$^4$ .................. A61K 37/02; C07K 7/08; C07K 7/10
[52] U.S. Cl. .................................. 514/13; 530/326
[58] Field of Search ........................ 514/13; 530/326

[56] References Cited

U.S. PATENT DOCUMENTS 4,428,941  1/1984  Galibert et al. .................. 514/2

OTHER PUBLICATIONS

Infection and Immunity (1981), 62–67, vol. 32, No. 1.
Proc. Nat'l Acad. Sci. U.S.A., vol. 78, No. 6, pp. 3824–3428 (1981).
Nature, vol. 290, (1981) 51–54.
Molecular Immunol., vol. 18, (1981), 869–72.
Proc. Nat'l. Acad. Sci., 76, 222–6 (1979).
Virology 17, 171–175 (1962).
J. of Virology (1968), 1482–4, vol. 2.
J. of Virology (1972), 182–3, vol. 9.
Science (1972), 1300–1301, vol. 178.
J. Gen. Virology (1973), 19, 129–134.
Experimental Hepatitis B. Polypeptide Vaccine in Chimpanzees (1978), 557–67.
J. of Biological Chem. 256, (1981), 6975–83.
The J. of Biol. Chem. 257, (1983), 7770–7.
Virol. Hepatitis (1981), 707–8.
Proc. Nat'l. Acad. Sci. 78, 3403–7 (1981).
Proc. Nat'l. Acad. Sci. 79, 579–82 (1982).
Chem. Abstract, vol. 79, (1973), 166–73.
Chem. Abstr., vol. 95, (1981), 12624.
Biol. Abstr., vol. 73, 61154 (1982).
Biol. Abstr., vol. 73, 17453 (1982).
Biol. Abstr., vol. 69, 51719 (1980).
Biol. Abstr., vol. 70, 16559 (1981).
Chem. Abstr., vol. 95, (1981) 95277u.
Chem. Abstr., vol. 92, (1980) 196139.
Chem. Abstr., vol. 93, (1980) 93303.
Chem. Abstr., vol. 99, (1983) 103597.
Chem. Abstr., vol 97, (1982) 37242.
Chem. Abstr., vol. 97, (1982) 160768.
Chem. Abstr., vol. 98, (1983) 32645.
Chem. Abstr., vol. 96, (1982) 18351.
Chem. Abstr., vol. 96, (1982) 102149.
Proc. Nat'l. Acad. Sci. 79, (1982), 4400–4.

Primary Examiner—Delbert R. Phillips
Attorney, Agent, or Firm—Cox & Smith Incorporated

[57] ABSTRACT

A composition for eliciting production of antibody to hepatitis B surface antigen and method of neutralizing the infectivity of hepatitis type B virus. A cyclic polypeptide is prepared having a disulfide bond in a hydrophilic region, namely residues 117–137 or 122–137 and an amino acid sequence unique from that associated with the native 25,000 molecular weight polypeptide derived from hepatitis B surface antigen.

12 Claims, 5 Drawing Sheets

Met - Glu - Asn - Ile - Thr - Ser - Gly - Phe - Leu - Gly - Pro - Leu - Leu - Val - Leu -
                                                      10                                30
- Gln - Ala - Gly - Phe - Phe - Leu - Leu - Thr - Arg - Ile - Leu - Thr - Ile - Pro - Gln -
         20                                                40
- Ser - Leu - Asp - Ser - Trp - Trp - Thr - Ser - Leu - Asn - Phe - Leu - Gly - Gly - Thr -
                         50                                                         60
- Thr - Val - Cys - Leu - Gly - Gln - Asn - Ser - Gln - Ser - Pro - Thr - Ser - Asn - His -
                                                      70
- Ser - Pro - Thr - Ser - Cys - Pro - Pro - Thr - Cys - Pro - Gly - Tyr - Arg - Trp - Met -
                         80                                                         90
- Cys - Leu - Arg - Arg - Phe - Ile - Ile - Phe - Leu - Phe - Ile - Leu - Leu - Leu - Cys -
                                                      100
- Leu - Ile - Phe - Leu - Leu - Val - Leu - Leu - Asp - Tyr - Glu - Gly - Met - Leu - Pro -
                         110                                                        120
- Val - Cys - Pro - Leu - Ile - Pro - Gly - Ser - Ser - Thr - Thr - Ser - Thr - Gly - Pro -
                                                      130
- Cys - Arg - Thr - Cys - Met - Thr - Thr - Ala - Gln - Gly - Thr - Ser - Met - Tyr - Pro -
                         140                                                        150
- Ser - Cys - Cys - Cys - Thr - Lys - Pro - Ser - Asp - Gly - Asn - Cys - Thr - Cys - Ile -
                                                      160
- Pro - Ile - Pro - Ser - Ser - Trp - Ala - Phe - Gly - Lys - Phe - Leu - Trp - Glu - Trp -
                         170                                                        180
- Ala - Ser - Ala - Arg - Phe - Ser - Trp - Leu - Ser - Leu - Leu - Val - Pro - Phe - Val -
                                                      190
- Gln - Trp - Phe - Val - Gly - Leu - Ser - Pro - Thr - Val - Trp - Leu - Ser - Val - Ile -
                         200                                                        210
- Trp - Met - Met - Trp - Tyr - Trp - Gly - Pro - Ser - Leu - Tyr - Ser - Ile - Leu - Ser -
                                                      220
- Pro - Phe - Leu - Pro - Leu - Leu - Pro - Ile - Phe - Phe - Cys - Leu - Trp - Val - Tyr - Ile

FIG. 1

```
                    Lys
                    122
                     |
                    Thr
                     |
    Ser — Cys  =  Cys — Met — Thr
     |     137   124            |
    Pro                        Thr
     |                          |
    Tyr                        Ala
     |                          |
    Met — Ser — Thr — Gly — Gln
```

PEPTIDE 1     MW = 1708

FIG. 2

```
              Lys — Ser — Pro — Gly — Thr — Ser
              122   121                       117
               |
              Thr
               |
    Ser — Cys = Cys — Met — Thr
     |         124            |
    Pro                       Thr
     |                         |
    Tyr                       Ala
     |                         |
    Met — Ser — Thr — Gly — Gln
```

PEPTIDE 2     MW = 2137

FIG. 3

| | 115 | 120 | 125 | 130 | 135 | 140 | 145 | 150 |
|---|---|---|---|---|---|---|---|---|
| Reference 29 ayw | Thr Ser Thr Gly Pro | Cys Arg Thr | Cys Met Thr Thr | Ala Gln Gly Thr | Ser Met Tyr Pro | Ser Cys Cys Cys Thr | Lys Pro Ser Asp Gly | Asn Ser Thr Cys Ile |
| Reference 30 assume adw | | Lys | Thr | Pro | Asn | Phe | Thr | |
| Reference 31 ady | Ser | | Thr | Pro | Ile | Thr | Ser | |
| Reference 8b and 8c adw ayw | | | Thr Thr | Pro Pro | Asn Thr | Phe Tyr | | |

FIG. 4

IDIOTYPES
A. Reaction of idiotype with specific epitope (HBs peptide)
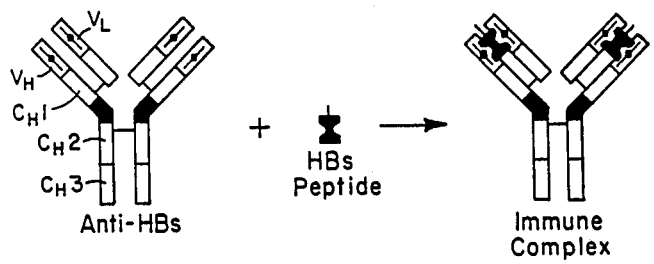
B. Blocking of idiotype with HBs antigen
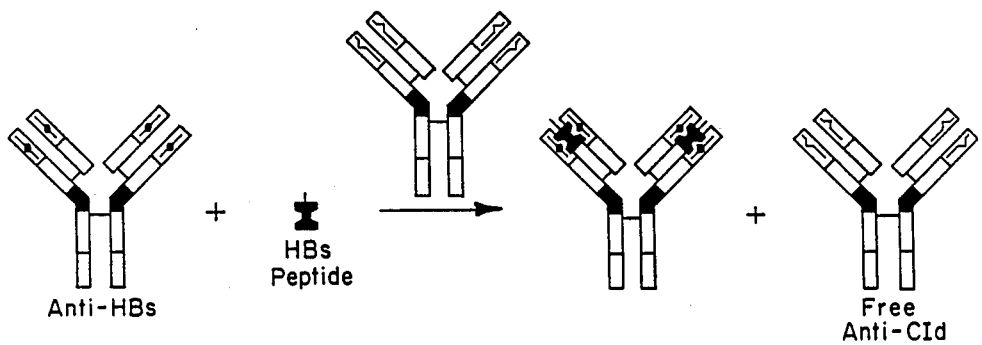
— ♦ — Antigen-Combining Site
— ⋈ — Specific HBs peptide
— ∨ — Anti-Idiotypic Antibody
FIG. 6

CYCLIC PEPTIDE AND METHOD OF USE FOR INDUCING AN IMMUNOLOGICAL RESPONSE TO HEPATITIS B VIRUS

The invention described herein was made during the course of work under grants from the National Heart, Lung and Blood Institute, National Institutes of Health, and the United States Army Medical Research and Development Command.

CROSS-REFERENCES TO RELATED APPLICATIONS

The present application is a continuation of application Ser. No. 1,120, filed on Jan. 7, 1987, now abandoned, which is a continuation of application Ser. No. 760,377 filed July 30, 1985, now abandoned, which is a continuation of application Ser. No. 447,722 filed Dec. 6, 1982, abandoned.

PRIOR ART STATEMENT AND BACKGROUND OF THE INVENTION

The following is an explanation of the background of the present invention together with a listing which, in the opinion of the Applicants, sets forth the closest prior art of which the Applicants are aware. A concise explanation of the relevance of the more important items is included.

Viral hepatitis has assumed significant world-wide epidemic proportions. It is estimated that there are two hundred million carriers of hepatitis B virus ("HBV") worldwide. The development of a conventional vaccine has been hampered by the inability to grow hepatitis B virus in tissue culture. As a result, it has been necessary to produce hepatitis B subunit particle vaccines by isolating and purifying the 22 nm lipoprotein particles composed of hepatitis B surface antigen ("HBsAg") from plasmas of asymptomatic human carriers. However, such formalin- or heat-inactivated vaccines have the disadvantages of substantial expense and limited supply. In addition, such a source presents potential hazards in view of unknown factors that may be present in the plasma. Also, as high-risk populations are immunized, sources of plasma containing large quantities of HBsAg will become scarce.

Chemically synthesized vaccines to replace viral vaccines offer the advantage of precise biochemical characterization, exclusion of genetic material of viral origin, exclusion of host- or donor-derived substances, consistent potency, and the like. Ideally, such synthetic vaccines do not have irrelevant microbial antigenic determinants, proteins or other materials that might otherwise contaminate the essential immunogen and cause unwanted side effects.

The possibility of a synthetic peptide vaccine for HBV has been suggested in the past. The following is a list of references relating to such vaccines or processes with respect thereto and which will be referred to herein by the respective reference numbers:

1. McAuliffe, V. J., Purcell, R. H. & Gerin, J. L. Rev. Infect. Dis. 2, 470–492 (1980).
2. Rao, K. R. & Vyas, G. N. Nature New Biol. 241, 240–241 (1973).
3. Melnick, J. L., Dreesman, G. R. & Hollinger, F. B. J. Infect. Dis. 133, 210–229 (1976).
4. Anderer, F. A. Biochim. Biophys. Acta 71, 246–248 (1963).
5. Fearney, F. J., Leung, C. Y., Young, J. D. & Benjamini, E. Biochim. biophys. Acta 243, 509–514 (1971).
6. Langbeheim, H., Arnon, R. & Sela, M. Proc. Natn. Acad. Sci. U.S.A. 73, 4636–4640 (1976).
7. Tiollais, P., Charnay, P. & Vyas, G. N. Science 213, 406–411 (1981).
8a. Peterson, D. L. J. Biol. Chem. 256, 6975–6983 (1981). 8b. Gavilaives, F., Gonzalez-Ros, F.M. & Peterson, D.L. J. Biol. Chem 257, 7770 (1982).
8c. Peterson, D. L. In Viral Hepatitis (Eds. W. Szmuness, H. J. Alter and J. E. Maynard). Franklin Institute Press, Philadelphia, p. 707 (1982).
9a. Lerner, R. A. et al Proc. Natn. Acad. Sci. U.S.A. 78, 3403–3407 (1981).
9b. Prince, A. M., Ikram, H. & Hopp, T. P. Proc. Natl. Acad. Sci. U.S.A. 79, 579 (1982).
9c. Bhatnagar, P. R., Papas, E., Blum, H. E., Milich, D. R., Nitecki, D., Karels, M. J. & Vyas, G. N. Proc. Natl. Acad. Sci. U.S.A. 79, 4400 (1982).
10. Chou, P. Y. & Fasman, G. D. Adv. Enzym. 47, 45–148 (1978).
11. Bull, H. B. & Breese, K. Archs Biochem. Biophys. 161, 665–670 (1975).
12. Atassi, M. Z. Immunochemistry 12, 423–438 (1975).
13. Merrifield, R. B. Adv. Enzym. 32, 221–296 (1969).
14. Edelstein, M. S., McNair, D. S. & Sparrow, J. T. in Peptides:Synthesis, Structure, Function (eds Rich, D. H. & Gross, E.) (Pierce Chemical Co., Rockford, pp. 217–220), 1981.
15. Sparrow, J. T. J. Org. Chem. 41, 1350–1353 (1976).
16. Atherton, E., Woolley, V. & Sheppard, R. C. JCS Chem. Commun., 970 (1981).
17. Mao, S. J. T., Sparrow, J. T., Gilliam, E. B., Gotto, A. M. & Jackson, R. L. Biochemistry 16, 4150–4156 (1977).
18. Felix, A. M., Jiminez, M. H., Wang, C. T. & Meienhofer, J. Int. J. Peptide Protein Res. 15, 342–354 (1980).
19. Dreesman, G. R., Hollinger, F. B., Sanchez, Y., Oefinger, P. & Melnick, J. L. Infect. Immun. 32, 62–67 (1981).
20. Sanchez, Y. et at Infect. Immun. 30, 728–733 (1980).
21. Dixon, W. J. & Brown, M. B. BMDP-79 (University of California Press, Berkeley, 1979).
22. Hollinger, F. B., Adam, E., Heiberg, D. & Melnick, J. L. in Viral Hepatitis (eds. Szmuness, W., Alter, H., & Maynard, J.) (Franklin Institute Press, Philadelphia, pp. 451–466, 1982).
23. Fudenberg, H. H. & Kunkel, H. G. J. Exp. Med. 106, 689–702 (1957).
24. Vyas, G. N. in Hepatitis B Vaccine (eds. Maupas, P. & Guesry, P.) (Elsevier, Amsterdam, 1981).
25. Hopp, T. P. & Woods, K. R. Proc. Natn. Acad. Sci. U.S.A. 78, 3824–3828 (1981).
26. Zuckerman, A. J. New Scient. 88, 167 (1980).
27. Skelly et al Nature 290, 51 (1981).
28. Hopp, T. P. Molec. Immun. 18, 869 (1981).
29. Charnay, P., Pourcel, C., Louise, A., Fritsch, A. and Tiollais, P. Proc. Natl. Acad. Sci. U.S.A. 76, 2222 (1979).
30. Valenzuela, P., Gray, P., Quiroga, M., Zaldivar, J., Goodman, A. M. and Rutter, W. J. Nature 280, 815 (1979).
31. Pasek, M., Golo, T., Gilbert W., Zink, B., Schaller, H., McKay, P., Leadbetter, G. and Murray, K. Nature 282, 575 (1979).

32. Allison, A. C., Buckland, F. E. and Andrewes, C. H. Virology 17, 171 (1962).
33. Carver, D. H. and Seto, D. S. Y. J. Virol. 2, 1482 (1968).
34. Hare, J. D. and Chan, J. C. Virology 34, 481 (1968).
35. Sukeno, N., Shirachi, R., Yamaguchi, J. and Ishida, N. J. Virol. 9, 182 (1972).
36. Vyas, G. N., Rao, K. R. and Ibrahim, A. B. Science 178, 1300 (1972).
37. Dreesman, G. R., Hollinger, F. B., McCombs, R. M. and Melnick, J. L. J. Gen. Virol. 19, 129 (1973).
38. Kohler, G. and Milstein C.: Continuous culture of fused cells secreting antibody of predefined specificity.
Nature (London) 256:495–497 (1975).
39. Oudin, J., and Michel, M. 1963. Une novelle formed' allotypie des globulines y du serum de lapin aparement lie'e a le jonction et a la specificite anticoyss. C. R. Seanc. Soc., Paris 257:805.
40. Hollinger, F. B., Dreesman, G. R., Sanchez, Y., abral, G. A. and Melnick, J. L. Experimental hepatitis B polypeptide vaccine in chimpanzees. In Viral Hepatitis (eds. G. N. Vyas, S. N. Cohen and R. Schmid). Franklin Institute Press, Philadelphia, pp. 557–567, 1978.

Reference 1 relates to formalin-inactivated hepatitis B virus vaccines that have been produced in several laboratories. The sole source of material for these vaccines has been 22-nm lipoprotein particles composed of HBsAg and derived from plasma of persons chronically infected with HBV.

The possibility of a synthetic peptide vaccine for HBV was suggested in References 2 and 3 following studies carried out with tobacco mosaic virus (References 4 and 5) and MS-2 coliphage (Reference 6). This possibility became a reality when the amino acid sequence for HBsAg was deduced from the nucleotide sequence of the cloned HBV genome as reviewed in Reference 7. Reference 8 discloses that a portion of the major polypeptide derived from HBsAg, with a calculated molecular weight of 25,000 (P25), has been sequenced.

Hepatitis B polypeptide vaccines containing hepatitis B-specific antigenic determinants associated with a non-glycosylated polypeptide with a molecular weight in the range 22,000–24,000 and a glycosylated polypeptide with a molecular weight in the range 26,000–29,000 have been prepared and tested for safety, immunogenicity and protective efficicacy in susceptible chimpanzees. (References 19, 26, 27 and 40). The non-glycosylated polypeptide and the glycosylated polypeptide referred to herein have molecular weights of 25,000 (P25) and 30,000 (GP30), respectively, as determined by their amino acid sequence deduced from the sequence of the cloned hepatitis B virus DNA genome. (Reference 7).

Previous studies have demonstrated that sulfhydryl groups and/or disulfide bonds play an important role in the tertiary structure of a number of animal viruses since biological activities such as infectivity and hemagglutination are destroyed by treatment with either alkylating (sulfhydryl binding) or reducing reagents (References 32–34). The differential effect of these different reagents is illustrated by the fact that a reducing agent such as dithiothreitol destroys the infectivity of many enteroviruses, but these same viruses are unaffected by treatment with sulfhydryl binding reagents (References 32, 33). More specifically, it has been shown that the antigenic determinants (epitopes) associated with HBsAg are conformation-dependent. This was demonstrated in that reduction of the disulfide bonds contained in HBsAg and subsequent alkylation of the free thiol groups destroyed both the antigenic and the immunogenic activities associated with HBsAg (References 35–37).

Reference 28 describes a computerized analysis of the amino acid sequences of the HBsAg protein to predict an antigenic site determinant. An amino acid sequence of residues 138–149 was synthesized and examined for its ability to bind antibodies to a mixture of the ad and ay subtypes of HBsAg. The peptide bound 9% of the antibodies.

As reported in Reference 9a, thirteen peptides were chemically synthesized corresponding to amino acid sequences predicted from the nucleotide sequence for HBsAg. Seven out of the thirteen synthetic peptides elicited an anti-peptide response in rabbits inoculated with three or four doses of a series of peptides, each containing 14–15 amino acid residues, but only after covalent linkage of the peptides to a carrier protein. Activity also was found after multiple injections of a peptide containing 34 amino acids. In Reference 9b a synthetic peptide containing amino acid residues 138–149 of P25 was prepared. This peptide was reported to contain the a group reactivity as well as d subgroup reactivity. When this peptide was conjugated to human erythrocytes and injected into mice, it induced the formation of anti-HBs with or without the use of Freund's adjuvant. The investigation in Reference 9c prepared seven linear peptide analogues of HbsAg: 122–137, 128–134, 139–147, 139–158, 140–158, 145–158, and 150–158. For experimental immunization of rabbits the synthetic peptides were coupled to keyhole limpet hemocyanin. The investigators studied the antigenicity of each peptide analogue by serologic neutralization of human antibodies specific for the a determinant of HBsAg. Analogues 139–147, 139–158, and 140–158 showed antigenicity as well as induction of anti-HBsAg. The rabbit antibodies were inhibited with each of the three peptide analogues and all serotypes of natural HBsAg, having only the a determinant in common. They reported that a linear form of peptide 122–137 and of peptide 128–134 covalent linked to a protein carrier failed to elicit production of anti-HBs in rabbits. (Reference 9c).

Two patent applications pertaining to the production of synthetic peptides with application to viral vaccines (with specific reference to HBsAg) have been noted. The first, by R. A. Lerner et al. (European Patent Application No. 044,710 filed July 16, 1981) describes the production of multiple synthetic peptides containing different amino acid sequences associated with the native P25 polypeptide derived from HBsAg. The Lerner et al. application differs from the present invention in two distinct areas. First, the Lerner et al. peptides are uniformly linear, and Lerner et al. made no attempt to produce tertiary conformation as described herein. Secondly, there was no attempt to purify the synthetic peptides before coupling to the protein carrier. Thirdly, Lerner et al. produced antibody to a peptide only after conjugation to a carrier. The antibody produced reacted with native HBsAg but no attempt was made to determine whether the linear peptides reacted with antibodies produced in human beings following a natural hepatitis B viral infection. As explained herein, the reaction of our circular peptide with human hepatitis B antibodies demonstrates the importance of cyclization of synthetic HBsAg peptides.

The second patent application by T. P. Hopp (European Patent Application No. 056,249 filed Jan. 8, 1982) describes the use of a computer program analysis modified to predict the most hydrophilic region of viral and bacterial polypeptides. He has applied this to the synthesis of a peptide containing 6 amino acid residues corresponding to amino acids 141-147 of the P25 protein of HBsAg. Similar to the teachings of Lerner et al. mentioned above, Hopp's peptides are uniformly linear and no attempt has been made to construct the tertiary structure associated with the conformation dependent antigenic determinants of HBsAg. Neither Lerner et al. nor Hopp mentions cyclization of their peptides by formation of intrachain or interchain disulfide bonds as in the present invention.

None of the above references teaches or suggests cyclic peptides containing disulfide bonds in a hydrophilic region of the major viral polypeptide which, as will be described hereafter, elicits an antibody response in mice after a single injection without linkage to a protein carrier. The composition according to the present invention contains a determinant that elicits the production of antibody of similar specificity to that produced by immunization with the SDS-denatured linear virus P25 polypeptide described in References 19 and 40. While the synthetic peptides disclosed in Reference 9a have several amino acids (138-146) in common with the compositions according to the present invention and there are four overlapping carboxyl amino acids of the peptides, there are no other substantial similarities between the teachings of References 9a,9b and 9c and the present invention.

SUMMARY OF THE INVENTION

The present invention is directed to (1) a new composition of matter, (2) a composition for use in an immunizing preparation, (3) a composition for eliciting production of antibody to HBsAg, (4) a method for eliciting production of antibody to HBsAg, (5) a method for determining whether the immunizing preparation (synthetic peptide) reacts with antibody in the host to a natural infection of the host, (6) a sensitive method to assess the reactivity of the synthetic peptide containing native conformation with natural antibody using anti-idiotype reagents, (7) a method to assess the reactivity of the synthetic peptide with monoclonal antibody prepared to the infectious agent, and (8) a new diagnostic method. The composition is a cyclic peptide containing a disulfide bond in a hydrophilic region of the major viral polypeptide P25. The composition results in immunogenicity shown by the detection of antibody activity in mice seven days after a single injection of the peptide, disulfide cyclization being important in locking the secondary structure of a potent immunogen.

It is, therefore, an object of the present invention to provide a composition comprising a cyclic polypeptide having a disulfide bond in a hydrophilic region of the peptide.

Another object is to provide such a conposition for use in any immunizing preparation specific to hepatitis B virus and/or for diagnostic use in connection therewith.

Another object of the present invention is the provision of such a composition for eliciting production of antibodies to hepatitis B surface antigen.

Another object of the present invention is the provision of a method to identify the relatedness of the cyclized synthetic peptide to antigenic determinants recognized by the host following a natural infection with the corresponding HBV.

Another object of the present invention is the provision of a method to identify antigenic determinants recognized by the host with the use of idiotype-anti-idiotype analysis.

Another object of the present invention is the provision of a method to identify the antigenic determinants recognized by the host with the use of monoclonal antibodies prepared to the native antigens of the infectious agent.

Yet another object of the present invention is the provision of a method for eliciting production of antibodies to HBsAg by introducing such a peptide into a host containing the antigen.

A still further object of the present invention is to provide a composition that will elicit protective antibodies against hepatitis B virus following immunization of humans.

Still other objects, features and advantages of the present invention will be apparent from the following description of the preferred embodiments of the invention, given for the purpose of disclosure and taken in conjunction with the accompanying drawings.

BRIEF DESCRIPTION OF THE DRAWINGS

FIG. 1 is an illustration of the generally accepted amino acid sequences of the major polypeptide derived from HBsAg with a calculated molecular weight of 25,000 (P25) as taught in Reference 7. The most hydrophilic regions as predicted by computer analysis (described in Reference 11) are single underlined.

FIG. 2 is an illustration of the amino acid sequences of a cyclic polypeptide according to the present invention wherein the disulfide bond occurs at residues 124-137 and is indicated by the symbol=. The peptide illustrated in FIG. 2 and described herein will be referred to as "peptide 1".

FIG. 3 is an illustration of the amino acid sequences of another cyclic peptide according to the present invention similar to that of FIG. 2 but containing five additional amino acid residues. The peptide illustrated in FIG. 3 and described herein will be referred to as "peptide 2".

FIG. 4 is an illustration of the amino sequence of a hydropilic region of P25 derived from the various subtypes of HBsAg. The sequence for ayw as taught in reference 29 was deduced from the sequence of the cloned HBV DNA genome. Amino substitutions were noted at several positions for adw and ayw subtype polypeptides (References 30 and 31, respectively). The amino acid residue substitutions noted in References 8b and 8c were deduced from amino acid sequence analyses of purified preparations of P25 polypeptides.

FIG. 6 illustrates what the applicants herein theorize is the basic mechanism of the idiotype system herein.

DETAILED DESCRIPTION OF THE PREFERRED EMBODIMENT

Figure 7:
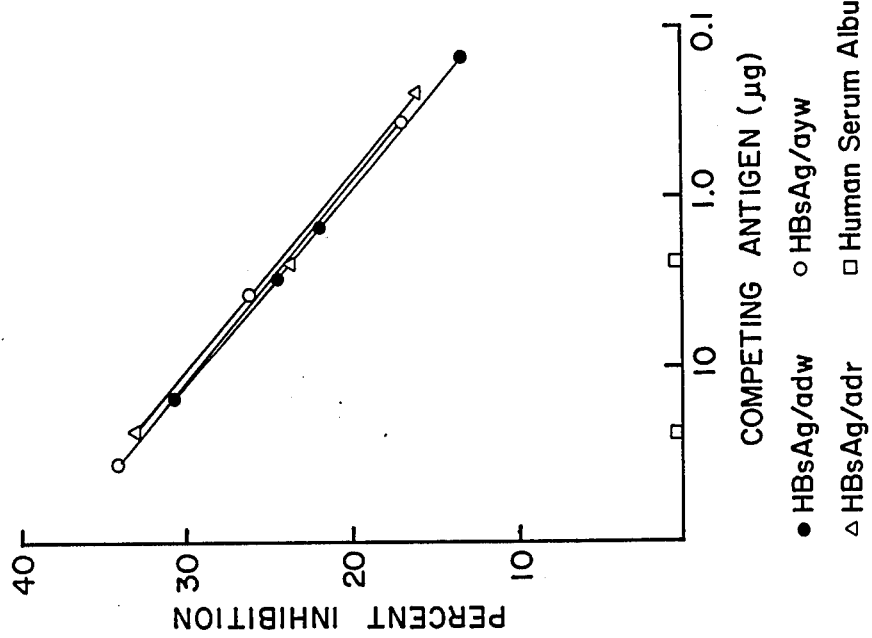
FIG. 7 graphically depicts inhibition of a human anti-HBs idiotype-anti-idiotype reaction c HBsAg subtypes adw, ayw and adr.
Figure 5:
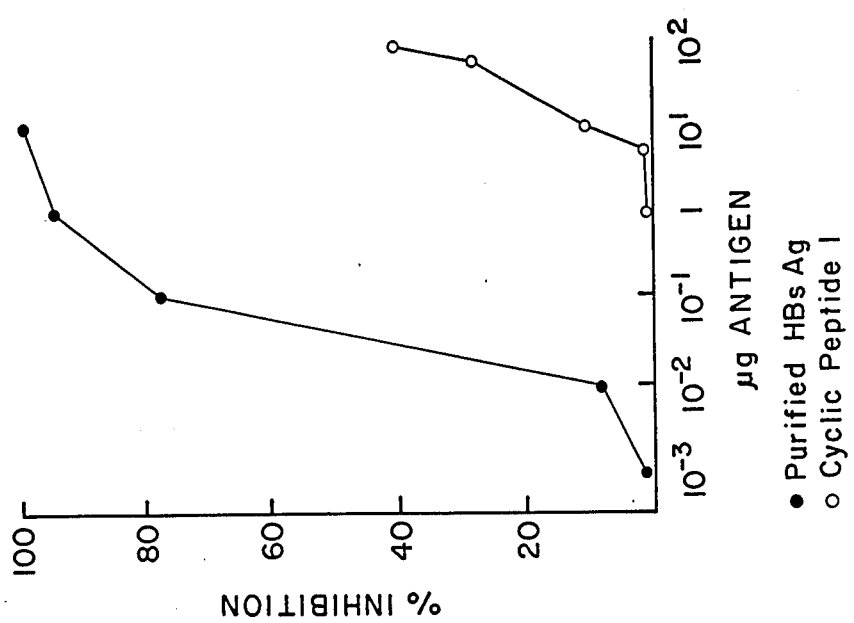
FIG. 5 graphically plots per cent inhibition of antibody to the a determinant of HBsAg by various concentrations of native HBsAg and cyclic peptide 1 to illustrate reactivity of a peptide as disclosed herein.

Using techniques disclosed in Reference 10, a computer analysis was made of the amino acid sequence of P25 to predict the secondary structure of the molecule to permit selection of the amino acid residues containing specific HBsAg determinants. A portion of the P25 molecule illustrated in FIG. 1 was sequenced as described in Reference 8a. The protein hydrophobicity was estimated using the amino acid assignments according to Reference 11. HBsAg was found to contain predominantly beta structure interrupted with a series of beta turns. Three highly hydrophobic regions were located between residues 1 and 42, 66 and 108, and 146 and 226, and two hydrophilic regions between residues 43 and 65, and 109 and 145. The latter hydrophilic regions are probably exposed on the intact particle and, consequently, beta turns in these regions represent potentially exposed antigenic determinants. The region between amino acids 117 and 137 was chosen for synthesis inasmuch as a single cyclic disulfide bond could be formed between Cys 124 and Cys 137 as illustrated in FIGS. 2 and 3 if a serine was substituted for the cysteine at position 121 in the ayw sequence as taught in reference 8a. Thus, by locking the conformation of the potential beta turns at residues 129–132 and 135–137, a polypeptide more native in structure could be obtained. Lysine was substituted for Arg 122 to provide a handle for cross-linking to other proteins, if needed, before injection into animals. The selected peptides were synthesized by solid-phase methodology according to References 13 and 15 on a Schwarz Bioresearch synthesizer modified for computer control according to Reference 14. Butyloxycarbonyl-S-p-methoxybenzyl-L-cysteine was coupled to p-hydroxy-methylphenylacetamidomethyl polystyrene using dicyclohexylcarbodiimide with a catalytic amount of 4-N,N-dimethylaminopyridine; the loading was 0.09 mM per g of resin. For the synthesis, the α-amino groups were protected with t-butyloxycarbonyl (t-BOC) and the side chain-protecting groups were as follows: benzyl ethers for the hydroxyl of serine and threonine, dichlorobenzyl ether for the phenolic hydroxyl of tyrosine and carbobenzoxy for the ε-amino group of lysine. Trifluoroacetic acid (40% in $CH_2Cl_2$) was used to remove the t-BOC protecting group, and the resulting salt was neutralized with N,N-diisopropylethylamine (5% in $CH_2Cl_2$). Dicyclohexylcarbodiimide was used to couple the t-BOC amino acids; hydroxybenzotriazole was added to the coupling reaction of glutamine to suppress side chain dehydration. The specific steps of the synthesizer program are described in References 15 and 17.

The protecting groups were removed and the peptide was cleaved from the resin at 0° C. with anhydrous hydrogen fluoride (HF) containing 10% anisole and 1% ethanedithiol as scavengers. The HF reagent was removed under vacuum at 0° C., and then the peptide was precipitated and washed with anhydrous ether. After extraction of the peptide from the resin with trifluoroacetic acid, the solvent was evaporated at 15° C. and the peptide again precipitated with ether. The ether was decanted after centrifugation and the pellet dissolved in 1M Tris/6M guanidine hydrochloride; the pH of this solution was immediately adjusted to 8. The solution was desalted on a BioGel P-2 column equilibrated in 0.1 M ammonium bicarbonate, and the peptide-containing fractions were pooled and lyophilized.

The cyclic disulfide was formed by oxidation of a dilute solution of the peptide with potassium ferricyanide according to the procedure of Reference 18. The solution was lyophilized, resuspended in ammonium bicarbonate and desalted on a BioGel P-2 column, and the peptide further purified by ion-exchange chromatography at 4° C. on a column of SP-Sephadex equilibrated in 0.02M $NaH_2PO_4$/6M urea, pH 3.74. The material eluted with a linear gradient of 800 ml of 0.02M $NaH_2PO_4$/6M urea and 800 ml of 0.15M NaCl/0.02 M $NaH_2PO_4$/6M urea, pH 3.74. The peptide was located by measuring the absorbance at 275 nm.

After desalting on Bio-Gel P-2 in ammonium bicarbonate and lyophilization, each peptide had the expected amino acid composition by amino acid analysis (Table 1) and eluted as a major peak on $C_{18}$-reversephase HPLC in a linear gradient of 1% triethyl ammonium phosphate, pH 3.2, and 2-propanol. The peptide was chromatographed on a column of Biogel P-10 precalibrated with a series of unrelated cyclic and linear peptides. Peptide 1 eluted at a volume expected for the cyclic form with a molecular weight of 1708. The linear form eluted at the smaller volume expected for a linear peptide of this size.

TABLE 1

Amino Acid Composition Of Synthetic Peptides

| Amino acid | Peptide 1 122–137 | Peptide 2 117–137 Ser 121 |
|---|---|---|
| Threonine* | 3.75(4) | 4.67(5) |
| Serine* | 1.93(2) | 3.55(4) |
| Glutamic acid | 1.06(1) | 1.06(1) |
| Proline | 0.85(1) | 1.92(2) |
| Glycine | 1.00(1) | 2.00(2) |
| Alanine | 0.99(1) | 1.08(1) |
| Half cystine** | — (2) | — (2) |
| Methionine | 1.87(2) | 1.87(2) |
| Tyrosine | 0.99(1) | 0.93(1) |
| Lysine | 0.93(1) | 0.92(1) |

Analyses were perfomed on a Beckman model 121 amino acid analyser after hydrolysis in vacuo for 24 h. at 110° C. in 6 M HCl. The theoretical values are given in parentheses.
*Values are not corrected for destruction during hydrolysis.
**Half cystine was present in the amino acid analysis but was not integrated.

P25 was derived from a purified preparation of HBsAg after solubilization by heating at 100° C. for 2 minutes in 0.5M urea/1% SDS/1% 2-mercaptoethanol (References 19 and 40). The soluble polypeptides were fractionated by cylindrical polyacrylamide gel electrophoresis ("PAGE") in 10% gels. The SDS-denatured linear P25 polypeptide, which is known to contain 226 amino acid residues, was used as a control for immunogenicity studies.

The two resulting synthetic peptides (117–137 of FIG. 3 and 122–137 of FIG. 2) were incorporated into a series of adjuvant vehicles for immunization of mice. Equal volumes of immunogen and Freund's complete adjuvant ("FCA") were emulsified to give a final peptide concentration of 50 μg per 0.4 ml. The alum-adsorbed preparations were prepared as described previously (References 19 and 40) with hydrated aluminum potassium sulfate, to give a final suspension containing 50 μg peptide per 0.4 ml. Large multilamellar liposomes were prepared from a mixture of dipalmitoylphosphatidylcholin cholesterol and dipalmitoylphosphatidic acid in a molar ratio of 2.0:1.5:0.2 respectively (per Reference 20). Dried lipid films were dispersed by vortexing in an aqueous medium at a phospholipid concentration of 20 mM. Liposomes were swollen in solutions containing either 100 μg of peptide per ml or 100 μg of peptide plus 1 mg ml$^{-1}$ muramyl dipeptide ("MDP"; Sigma). To ensure that comparable doses were given in each case, untrapped antigen was not removed. Previous studies reported in Reference 20 have indicated that about 60% of HBsAg materials were associated with liposomes prepared in these conditions. Final liposome concentrations were adjusted such that each animal received 6 mmol phospholipid and 25 μg peptide with or without 250 μg MDP in a volume of 0.3 ml.

Groups of six female BALB/c mice were immunized intraperitoneally with each of the above preparations. The mice were bled from the tail vein on days 7, 14 and 21. Samples were assayed at a serum dilution of 1:4 using a commercial solid-phase radioimmunoassay (AUSAB, Abbott, North Chicago). Anti-HBs concentrations are expressed in Table 2 as milli-International Units per millilitre (MIU ml$^{-1}$) based on the international reference preparation of anti-HBs (lot 26.1.77) provided by the International Laboratory for Biological Standards, Central Laboratory of the Netherlands Red Cross Transfusion Service. A computer nonlinear regression program, BMDP3R (per Reference 21), was used to describe the standard dose-response curve for the World Health Organization ("WHO") international reference preparation from which the potency of each of the samples was obtained.

TABLE 2

Anti-HBs concentrations in mice immunized with 25 μg synthetic HBsAg peptides 117-137 (FIG. 3) and 122-137 (FIG. 2)

| Immunizing preparation | Range of antibody concentration postinjection (mIU ml$^{-1}$) | | |
|---|---|---|---|
| | Day 7 | Day 14 | Day 21 |
| 117-137-FCA | 3.5–8.6(4/6)[a] | 3.2–10.3(5/6) | 2.6–13.9(5/6) |
| 122-137-FCA | 3.6–5.8(3/6) | 5.9–11.9(3/6) | 17.3–25.9(3/6) |
| 117-137-alum | 3.0–7.3(2/6) | 2.8–12.6(3/6) | 3.4–4.5(2/6) |
| 122-137-alum | 2.1–14.5(4/6) | 2.5–10.0(3/6) | 5.0–6.4(2/6) |
| 117-137-liposomes | 2.1–15.4(3/6) | 2.0–12.8(4/6) | — |
| 122-137-liposomes | 3.6–8.8(3/6) | 5.2–12.0(3/6) | 5.6–11.8(3/6) |
| 122-137-liposomes + MDP | 2.1–23.7(4/6) | 2.9–21.0(3/6) | 6.8–40.0(2/6) |
| P25 polypeptide-alum | 2.1–17.2(6/6) | 2.5–10.5(3/6) | 7.1–12.5(2/6) |

[a]Only positive antibody values are listed. Numbers in parentheses represent number of mice with an anti-HBs response over total number of mice in each group.

The results given in Table 2 show that (1) approximately 50% of the mice in each group produced detectable levels of antibody 7 days after inoculation with either the synthetic peptides or the P25 polypeptide; (2) the adjuvant vehicle—FCA, alum, liposomes, or liposomes with incorporated of MDP—did not significantly affect the primary antibody response; (3) in several groups the antibody response was greater on day 14, as shown by either the increased anti-HBs concentrations or the number of mice in each group which responded; (4) on day 21, the peak levels of antibody response in most groups of mice decreased; and (5) the antibody response in mice inoculated with purified SDS-denatured P25 was similar to that observed with the synthetic peptides.

When sera from each group of positive mice on days 7, 14 and 21, respectively, were pooled and fractionated by ultracentrifugation in 10–40% (w/v) preformed sucrose gradients (per Reference 23),IgG antibody was localized in the intermediate fractions and IgM was detected in the rapidly sedimenting fractions. Typical IgM and IgG responses were seen in each group, with one exception: there was no IgG in the group of mice injected with peptide 122-137 (peptide 1) emulsified with FCA.

Two procedures were used to enhance the immunogenic activity of cyclic peptide 1 (amino acid residues 122-137) by methods that would be acceptable for field trials in humans. The first involved preparation of peptide micelles similar to those described previously for virus proteins. The second procedure involved the covalent linking of tetanus toxoid to peptide 1.

The peptide micelles were prepared by incubating 500 μg of peptide 1 suspended in 0.01M Tris-HCl, 0.5M NaCl, pH 7.3, with a final concentration of 2% Triton X-100 at 37° C. for 18 hours. Approximately 200,000 counts per minutes (cpm) of $^{125}$I-labeled peptide 1 was added as tracer before the detergent treatment. The mixture was then layered on a Triton X-100 free 10–50% weight per volume (w/v) preformed sucrose gradient and centrifuged at 36,000 rpm for 72 hours in a Beckman SW41 rotor. Two peaks of radioactivity were detected: a minor peak located in the first fraction (top of gradient), and a major band (containing >80% of the total label material) at approximately one-third the distance from the top of the gradient. Examination of the latter peak by electron microscopy revealed the presence of pleomorphic aggregates with diameters ranging from 40 to 80 nm. These aggregates sedimented more slowly and had a lower density (1.10 g/cm$^3$ in sucrose) than that observed when micelles were prepared from solubilized 22-nm HBsAg particles (1.19 g/cm$^3$ in sucrose). The peptide micelle preparation was dialyzed against 0.01M Tris-HCl buffer, pH 7.2, for 18 hours at 4° C.

Peptide 1 and purified tetanus toxoid were conjugated using a modified carbodiimide method. Briefly, 500 μg of peptide was incubated with 5 mg of 1-ethyl-3-(3'-dimethylaminopropyl) carbodiimide-HCl (Sigma Chemical Co., St. Louis, Mo.) in 0.0125 M Na-phosphate buffer, pH 5.0, for 2 minutes at 22° C. The pH of the mixture was adjusted to 8.0 with 0.1M NaOH. 3 ml of tetanus toxoid (Connaught Laboratories, Swiftwater, Pa.) containing 8 Lf/1500 μg protein/ml was subsequently added and allowed to interact for 18 hours at 22° C. The resulting conjugate was dialyzed for 24 hours at 4° C. against several changes of 0.1M sodium phosphate buffered saline (0.15M NaCl), pH 8.0.

The two preparations, peptide micelles and peptide-tetanus toxoid conjugate, were tested for immunogenicity in mice either as an aqueous suspension or after adsorption to alum gel. Alum precipitation of both vaccines was carried out as previously described. The final preparations of aqueous material and of alum gels were diluted in 0.15M NaCl containing 0.01M phosphate, pH 7.2, to contain 10 μg peptide/200 μl. For each vaccine, a group of 6 BALB/c mice received an intraperitoneal primary inoculation of 10 μg peptide. Mice were bled from the tail vein prior to inoculation and 7, 14, 21 and 32 days postinoculation. All sera were diluted 1:6 in 0.01M PBS, pH 7.2, and tested for anti-HBs activity by the AUSAB solid phase radioimmunoassay. The results were reported as the ratio of the cpm of each serum sample (S) divided by the cpm obtained with a pool of the normal sera (N) obtained from the same group of mice before the primary inoculation. A 1:6 diluted serum sample with an S/N value ≧2.1 was considered positive.

The relative immunogenicity of each preparation, illustrated by the number of mice developing an anti- HBs response, is summarized in Table 3. Similar to earlier observations, a proportion of mice in each group responded with low levels of specific anti-HB activity (S/N values ranging from 2.7 to 9) as early as 14 days after the primary inoculation. It should be noted that these mice received only 10 μg peptide 1 (versus 25 μg injected previously) and the starting serum dilution was 1:6 rather than 1:4. Bearing this in mind, the response was not better than had been noted after injection of BALB/c mice with liposome entrapped uncoupled peptide 1. The weakest immune response was noted in the group of mice immunized with peptide micelles in saline; only 1 of 6 mice produced a detectable level of antibody.

TABLE 3

Immunogenicity of 10 μg peptide 1 (amino acid residues 122–137) in micelle form or with a tetanus toxoid carrier

| | Immunogen | | | |
|---|---|---|---|---|
| | peptide micelles (saline) | peptide micelles (alum) | peptide-tetanus toxoid (saline) | peptide-tetanus toxoid (alum) |
| Preinoculation | 0/6* | 0/6 | 0/6 | 0/6 |
| Days after primary inoculation | | | | |
| 7 | 0/6 | 0/6 | 0/6 | 0/6 |
| 14 | 1/6 | 1/6 | 2/6 | 1/6 |
| 21 | 1/6 | 1/6 | 4/6 | 2/6 |
| 32 | 0/6 | 2/6 | 3/6 | 1/6 |
| Days after booster | | | | |
| 13 | 3/6 | 4/5 | 3/6 | 5/6 |
| 32 | 1/6 | 4/5 | 4/5 | 6/6 |

*No. of mice responding/no. of mice inoculated. All sera were tested at a 1:6 dilution using an AUSAB kit. Sera with S/N values ≧2.1 were considered positive.

Thirty three days after the primary immunization, the mice were boostered with 50μg of peptide in the respective vaccine preparations. The animals were bled at 13 and 32 days after booster, and the sera were tested for anti-HBs as described above. An anamnestic response was noted in all four groups of animals, in terms of percentage of responding animals (Table 3) and levels of antibody titers. As saline preparations, peptide micelles were a poor immunogen but the tetanus toxoid conjugate was a strong immunogen. Adsorption on alum gel greatly increased the immunogenicity of the micelle preparation, while only slightly enhancing the immune response to the peptide-tetanus toxoid conjugate. It is noteworthy that 80–100% of the mice possessed detectable levels of anti-HBs 32 days after the booster inoculation of peptide micelles adsorbed on alum gel and of peptide-tetanus toxoid in either saline solution or alum gel form (Table 3).

Fifty percent of the animals injected with peptide micelles adsorbed on alum and peptide-tetanus toxoid in saline produced antibodies that yielded S/N ratios of 10 or greater (at a serum dilution of 1:6) and 5 of 6 animals injected with peptide-tetanus toxoid-alum were positive at these levels (Table 4).

TABLE 4

Anti-HBs activity 32 days after a booster inoculation of mice with peptide 1 in micelle form or with a tetanus toxoid carrier

| | Immunogen | | | |
|---|---|---|---|---|
| Respective mouse number in each group | peptide micelles (saline) | peptide micelles (alum) | peptide-tetanus toxoid (saline) | peptide-tetanus toxoid (alum) |
| 1 | <2.1* | 14 | 20 | 123 |
| 2 | 2.7 | 22 | <2.1 | 27 |
| 3 | <2.1 | 76 | 153 | 96 |
| 4 | <2.1 | ND** | 18 | 10 |
| 5 | <2.1 | 7.5 | 3.4 | 25 |
| 6 | <2.1 | <2.1 | ND | 2.1 |

*S/N ratio determined using an AUSAB kit, at a 1:6 serum dilution. Sera with S/N values ≧2.1 were considered positive.
**ND = not done due to death of mouse.

The above observations demonstrate that a cyclic synthetic peptide analogous to amino acid positions 122 through 137 of P25 induces high levels of specific anti-HBs in mice. Although a primary response was noted in animals immunized with peptide 1 entrapped in liposomes, the anamnestic response was poor (data not shown). It appears that a peptide with a molecular weight of approximately 2,000 must be in an aggregated form, such as micelles, or must be linked to a protein carrier to efficiently recruit memory B cells.

Two tools have been developed and utilized to obtain data on the particular epitopes associated with the cyclic peptides. The first tool employed a panel of monoclonal anti-HBs antibodies to analyze the epitopes associated with peptide 1. The monoclonal antibody technique, originally developed by Kohler and Milstein (Reference 38), involves the establishment of a clone of lymphocytes, termed hybridomas, that produces homogenous antibody to a single epitope.

The epitope(s) associated with the synthetic cyclic peptide 1 (SP1) was initially analyzed using a panel of 14 anti-a monoclonal antibodies. None of these monoclonal preparations displayed any detectable reaction with either human serum albumin or human IgG. All reacted with purified particles of three different HBsAg subtypes: adw, ayw and adr (Tables 5 and 6). The anti-a specificity was further substantiated in that preincubation of each monoclonal antibody with purified HBsAg, subtype adw or ayw, decreased antibody binding to any HBsAg subtype on the solid phase by greater than 70%.

TABLE 5

Reaction of cyclic peptide 1 with anti-a monoclonal antibodies

| Monoclonal Antibody | Coating HBsAg Subtype | Counts Bound Without Inhibitor | % Inhibition of Binding* after Blocking with: | |
|---|---|---|---|---|
| | | | 80 μg Cyclic peptide 1 | 6 μg HBsAg/adw |
| A-1 | adw | 2074 | 9.7 | 100 |
| | ayw | 1531 | 4.7 | 96 |
| | adr | 1343 | 6.1 | 95 |
| A-2 | adw | 1993 | 35.7 | 100 |
| | ayw | 1709 | 42.4 | 100 |
| | adr | 1555 | 87.7 | 100 |
| A-4 | adw | 1368 | 34.0 | 91 |
| | ayw | 689 | 63.6 | 100 |
| | adr | 1341 | 31.2 | 91 |
| A-6 | adw | 2809 | 0 | 97 |
| | ayw | 1944 | 0 | 100 |
| | adr | 1674 | 6.2 | 100 |
| A-7 | adw | 2647 | 0 | 95 |
| | ayw | 1989 | 2 | 100 |
| | adr | 1782 | 0 | 99 |
| A-8 | adw | 1042 | 0 | 100 |
| | ayw | 1762 | 10.5 | 100 |
| | adr | 1429 | 0 | 100 |

TABLE 5-continued

Reaction of cyclic peptide 1 with anti-a monoclonal antibodies

| Monoclonal Antibody | Coating HBsAg Subtype | Counts Bound Without Inhibitor | % Inhibition of Binding* after Blocking with: | |
|---|---|---|---|---|
| | | | 80 μg Cyclic peptide 1 | 6 μg HBsAg/adw |
| A-10 | adw | 2272 | 0 | 100 |
| | ayw | 1561 | 0 | 98 |
| | adr | 1988 | 0 | 94 |
| A-11 | adw | 1267 | 0 | 100 |
| | ayw | 1734 | 1.8 | 100 |
| | adr | 1995 | 1.9 | 100 |
| A-12 | adw | 1438 | 67.0 | 100 |
| | ayw | 1987 | 66.8 | 100 |
| | adr | 1573 | 54.7 | 100 |
| A-13 | adw | 1407 | 47.2 | 100 |
| | ayw | 1742 | 51.8 | 80 |
| | adr | 1770 | 42.7 | 96 |
| A-14 | adw | 1078 | 15.2 | 100 |
| | ayw | 986 | 2.6 | 100 |
| | adr | 1231 | 13.5 | 91 |
| A-15 | adw | 1774 | 21.8 | 100 |
| | ayw | 1464 | 23.2 | 100 |
| | adr | 1389 | 32.1 | 90 |
| A-16 | adw | 878 | 0 | 100 |
| | ayw | 1979 | 0.2 | 98.5 |
| | adr | 668 | 0 | 90 |
| Hyb-1 | adw | 3353 | 0 | 100 |
| | ayw | 3730 | 5.0 | 99 |

*Measured by the ability of cyclic peptide 1 or HBsAg to inhibit the binding of each monoclonal antibody to a solid phase coated with various HBsAg. Values of ≧15.0% were considered as positive.

Based on the above experiments, the anti-a monoclonal antibodies were similarly tested against constant amounts of cyclic peptide 1 (80 μg/test) and HBsAg-/adw (6 μg/test). As shown in Table 5, 80 μg of cyclic peptide 1 inhibited the reactivity of 6 of the 13 monoclonal antibodies between 13.5 and 87.7%. Individual monoclonal antibodies displayed different levels of inhibition: A-14 and A-15 were inhibited from 13 to 32%, whereas A-2, A-4, A-12 and A-13 were inhibited from 31 to 87%. These levels of inhibition were reproducible in repeat experiments. The group a specificity of the cyclic peptide 1 was also demonstrated in that preincubation with the peptide decreased the reactivity of an antibody with each of the three HBsAg subtypes used as coating antigen (Table 5). 6 μg of HBsAg/adw inhibited the anti-a reactivity of all 13 monoclonal preparations by greater than 90%.

The role of conformation in regard to the a antigenic activity of peptide 1 was demonstrated by retesting selected anti-a monoclonal preparations for their ability to react with linear peptide 1. Linear peptide 1 was obtained by reduction of the intrachain disulfide bond of cyclic peptide 1 and subsequent alkylation of the free thiol groups. Five monoclonal antibodies that failed to react with cyclic peptide 1 also did not react with the linear form. Two monoclonal antibodies that reacted with cyclic peptide 1 (A-2 and A-12) failed to exhibit a significant level of reacivity with linear peptide 1. The level of reactivity of A-13 with linear peptide 1 was markedly reduced. One exception was noted; monoclonal antibody A-4 was inhibited to a significant degree with both the cyclic and linear forms of the peptide (Table 6).

TABLE 6

Reaction of cyclic and linear peptide 1 with anti-a monoclonal antibodies

| Monoclonal Antibody | Coating HBsAG Subtype | Counts Bound Without | % Inhibition of Binding* after blocking with: 80 μg Cyclic Peptide 1 | 80 μg Linear Peptide 1 | 6 μg HBsAg/adw | 6 μg HBsAg/ayw |
|---|---|---|---|---|---|---|
| A-2 | adw | 901 | 43 | 6 | 97 | 92 |
| A-4 | adw | 2567 | 31.8 | 28.8 | 100 | ND |
| A-12 | adw | 5162 | 41 | 0 | 99 | 99 |
| | ayw | 5728 | 57 | 0 | 99 | 100 |
| A-13 | adw | 2321 | 47 | 17 | 96 | 96 |
| | ayw | 2439 | 28 | 0 | 70 | 98 |

*Measured by the ability of peptide 1 or HBsAg to inhibit the binding of each monoclonal antibody to a solid phase coated with HBsAg.

The reactivity of the cyclic peptide 1 was examined further by incubating increasing quantities of the peptide with A-12 monoclonal antibody and subsequently testing the residual anti-a activity against HBsAg/adw by a micro-SPRIA test. As a control for this assay, the monoclonal antibody was also incubated with various concentrations of HBsAg, subtype adw. As shown in FIG. 5, 6 μg of intact HBsAg particles abolished all anti-a activity of monoclonal A-12. Inhibition values ranged from 8 to 96% with HBsAg concentrations of 0.01 to 1 μg, respectively. Cyclic peptide 1 also blocked anti-a activity of A-12; however, compared on a weight basis to HBsAg, a 3000-fold excess of cyclic peptide 1 was necessary to achieve an equivalent degree of inhibition (FIG. 5).

Three monoclonal antibodies previously characterized as reacting preferentially with the y subtype epitope (Y-3, Y-2 Hyb-2) were incubated with cyclic and linear peptide 1 and then tested for residual anti-HBs activity, utilizing HBsAg subtypes adw, ayw and adr as coating antigens. All three antibody preparations reacted with both cyclic and linear peptide 1 (Table 7). At high concentrations of Y-2 and Hyb-2 (dilutions of $10^{-1}$ and $10^{-4}$, respectively), inhibition was noted only with linear peptide 1, whereas at a 10-fold lower concentration of antibody each form of the peptide inhibited at similar levels.

TABLE 7
Reaction of cyclic and linear peptide 1 with anti-y and anti-w monoclonal antibodies

| Monoclonal Antibody (Dilution) | Coating HBsAg Subtype | Counts Bound Without Inhibitor | % Inhibition of Binding* after blocking with: | | | |
|---|---|---|---|---|---|---|
| | | | 80 μg Cyclic Peptide 1 | 80 μg Linear Peptide 1 | 6 μg HBsAg/ adw | 6 μg HBsAg/ ayw |
| Y-3 (10$^{-1}$) | adw | 166 | —** | — | — | — |
| | ayw | 2554 | 17.5 | 23.8 | 0 | 98 |
| | adr | 1677 | 6 | 3 | 0 | 100 |
| (10$^{-2}$) | ayw | 870 | 31.2 | 31.0 | 0 | 95.4 |
| | adr | 472 | 0 | 0 | 0 | 100 |
| Y-2 (10$^{-1}$) | adw | 234 | — | — | — | — |
| | ayw | 2358 | 4 | 27 | 4.2 | 93 |
| | adr | 161 | — | — | — | — |
| (10$^{-2}$) | ayw | 1939 | 37.5 | 23.5 | 6.9 | 98.9 |
| (10$^{-3}$) | ayw | 735 | 46.8 | 40.4 | 1.8 | 100 |
| Hyb-2(10$^{-4}$) | adw | 43 | — | — | — | — |
| | ayw | 1576 | 1.3 | 20 | 0 | 100 |
| | adr | 2203 | 1.2 | 3.5 | 0 | 100 |
| (10$^{-5}$) | ayw | 730 | 24 | 20.4 | 7.2 | 97.9 |
| | adr | 719 | 0 | 0 | 0 | 100 |
| W-1 | adw | 1278 | 0.8 | ND** | 92 | ND |
| | ayw | 1879 | 0.3 | ND | 87 | ND |
| | adr | 258 | — | — | — | — |

*Measured by the ability of peptide 1 or HBsAg to inhibit the binding of each monoclonal antibody to a solid phase coated with various HBsAg subtypes.
**(—) indicates that these monoclonal antibodies failed to react with the respective coating HBsAg subtype and consequently inhibition could not be tested.
***ND = not done.

It was noteworthy that two of the three anti-y preparations (Y-3 and Hyb-2) reacted with both ayw and adr coating antigens in the absence of inhibitors and that intact ayw particles blocked completely their reactivity with these two coating HBsAg subtypes (Table 7). However, linear and cyclic Sp1 blocked only the reactivity with the ayw coating antigen.

The final analysis was performed with a monoclonal antibody that recognized the w subtype epitope. No inhibition of reactivity was observed upon incubation of this antibody with cyclic peptide 1 (Table 7).

These studies demonstrate that the group a crossreactivity associated with HBsAg contains 2 or more distinct antigenic determinants and that the peptide contains one of these epitopes. The demonstration that a conformationdependent group a epitope is associated with peptide 1 is important since a series of observations, both in humans and in experimentally infected chimpanzees, has demonstrated that antibody to the group a antigenic determinant produces immunity to all HBV subtypes: adw, adr, ayw, ayr. In addition, peptide 1 also contains a sequential y epitope.

The second immunochemical tool used to determine the ability of peptide 1 to elicit protective antibody resided with the idiotypic specificity of the anti-HBs antibodies produced by HBV-infected humans. The basic concept of the idiotypic system is illustrated in FIG. 6. The region associated with the variable region ($V_L$ and $V_H$) of the immunoglobulin (Ig) molecule and which contains the antigencombining site has been defined by Oudin (Reference 39) as the idiotype of that Ig molecule. An anti-idiotype reagent is produced by injection of a second species, such as rabbits, with specifically purified antibody, e.g., human anti-HBs. The resulting rabbit antiserum is extensively adsorbed with normal human Ig negative for anti-HBs reactivity. The antiidiotype antiserum (with ⎯⎯ regions) thus recognizes only that region of the IgG molecule (shown as --●--) which specifically reacts with HBsAg. It has been found that humans infected with HBV generate anti-HBs which contains a common idiotype (CId).

Thus, it is possible that the CId associated with human anti-HBs antibodies may be blocked from reacting with a specific anti-Id reagent by prior incubation with either HBsAg or with peptide 1 if the peptide is antigenically related to HBsAg. (See FIG. 6B for experimental design.) The CId was found to be associated with the a group specificity in that purified 22-nm particles of adw, ayw, and adr specificities inhibited the CId-anti-idiotype reaction to the same degree (FIG. 7). Both peptide 1 and peptide 2 efficiently inhibited the reaction. Inhibition was also obtained with a nondenatured HBsAg polypeptide (P25-GP30) micelle preparation (Table 8). The major role of conformation was emphasized in that reduction of the disulfide bond and alkylation of the free thio groups not only produced a linear peptide but also destroyed its capacity to block the CId-anti-idiotypic reaction (Table 8). Similarly, SDS-denatured preparations of P25 and GP30 also only partially inhibited the reaction providing further evidence that secondary structure is important in producing a potent immunogen.

In another series of experiments designed to further support our claims that the cyclic peptide 1 is antigenically related to antigenic determinants associated with HBsAg which elicit production of anti-HBs in humans, anti-HBs monoclonal antibodies were examined for the ability to inhibit the binding of the common idiotype to its respective anti-idiotype antiserum. Monoclonal antibodies that reacted with cyclic peptide 1 also were found to partially inhibit the common anti-HBs idiotype-anti-idiotype reaction (Table 9). Conversely, no inhibition was noted using monoclonal antibodies that failed to react with cyclic peptide 1. Thus, antibody preparations A-2, A-4, A-12 and Y-2 inhibited the idiotype-anti-idiotype reaction by greater than 22%, while A-16 and W-2 failed to demonstrate a significant level of inhibition. Mouse ascites fluid containing monoclonal antibodies with specificity for herpes simplex virus also failed to inhibit the common anti-HBs idiotype-anti-idiotype reaction, indicating that a 20% level of inhibition was not due to nonspecific reactivity.

TABLE 8

Percent Inhibition of the Common Anti-HBs Idiotype Binding Its Anti-Idiotype Antiserum by Different Concentrations of Various Inhibitors

| Inhibitor | Concentration (μg) | Inhibition |
| --- | --- | --- |
| Native HBsAg-derived polypeptide | 7.5 | 63 |
| | 3.75 | 45 |
| | 0.75 | 21 |
| | 0.375 | 18 |
| Native HBsAg-derived polypeptide, reduced and alkylated | 7.5 | 2 |
| | 0.75 | 0 |
| | 0.075 | 0 |
| SDS-denatured P25 and GP30 | 25.0 | 9–13 |
| | 2.5 | 2–5 |
| Synthetic peptide 1 | 250 | 63 |
| | 25 | 33 |
| | 2.5 | 30 |
| Synthetic peptide 1, reduced and alkylated | 25 | 1 |
| | 2.5 | 0 |
| Human serum albumin | 20.0 | 0 |
| | 5.0 | 0 |

TABLE 9

Inhibition pattern of monoclonal antibodies in association with cyclic peptide 1 or with a CHBs idiotype

| Monoclonal Antibody | Epitope Specificity | % Inhibition | |
| --- | --- | --- | --- |
| | | Cyclic Peptide 1* | Common Anti-HBs Idiotype** |
| A-2 | a | 36–88 | 24 |
| A-4 | a | 31–64 | 25 |
| A-12 | a | 55–67 | 26 |
| A-16 | a | 0 | 0 |
| Y-2 | y | 40–47 | 22 |
| W-1 | w | 0 | 0 |

*The cyclic peptide was utilized to inhibit the reaction between the monoclonal antibody and HBsAg-coated wells.
**The monoclonal antibody was utilized to inhibit the common anti-HBs idiotype-anti-idiotype reaction.

The premise that the cyclic peptide 1 contains a epitope similar to that which is recognized by the host following a natural infection by HBV is supported by the following study. A chimpanzee which had developed anti-HBs in response to an HBV infection, was inoculated with a conjugate of peptide 1 covalently linked to tetanus toxoid. Four weeks post-inoculation, the anti-HBs titer rose to 1:6560 from a base line level of 1:1160 as determined by radioimmunoassay (AUSAB). Thus, a booster response was noted to an epitope for which the host had prior immunological memory.

Several methods are available to optimize the conjugation protocols for coupling a synthetic peptide to a carrier protein. For instance (1) peptide 1 may be conjugated in varying molar ratios to tetanus toxoid through the free carboxyl group of the cysteine residue at position 137; (2) peptide 1 also may be conjugated in varying molar ratios to tetanus toxoid through the ε-amino group of the lysine residue at position 122; and (3) polymers of cyclic peptide 1 may be prepared by linking the position 137 carboxyl group to the ε-amino group of lysine 122.

Peptide 1 has been used as a diagnostic model for the detection of anti-HBs antibodies by cross-linking the peptide to polylysine using the carbodiimide procedure described above. This conjugate was used to coat micro wells of a 96-well polystyrene plate. Each micro-titer well was incubated with a variety of serum dilutions containing anti-HBs. Specific reaction of these antibodies was detected by the addition of specific $^{125}$I-labeled antiglobulin reagents. The results indicate that this protocol provides a highly sensitive and specific method for the detection of anti-HBs antibody. It follows that cyclic synthetic HBsAg peptides attached to a detectable probe can be used in competitive binding assays to detect HBsAg in clinical specimens similar to methods commonly used to measure small peptide hormone reactants.

Early work with a plant virus model using tobacco mosaic virus (References 4 and 5) and the bacterial virus model using MS-2 coliphage (Reference 6) has clearly demonstrated the immense potential of preparing immunologically active synthetic peptide analogues to amino acid sequences found in an animal virus protein. The present results indicate that amino acid residues localized in the major HBsAg polypeptide, P25, between residues 117 and 137—or more specifically, 122 and 137—contain a determinant that elicits the production of antibody of similar specificity to that produced following immunization with the SDS-denatured HBsAg P25 polypeptide as reported in References 19 and 40. These results are similar to those reported recently in Reference 9 which reports preparation of a series of linear synthetic peptides containing segments of the P25 HBsAg polypeptide. Four of the peptides (2–16, 22–35, 48–81 and 95–109) reported in Reference 9 elicited the production of antibody in rabbits which reacted with HBsAg. Synthetic peptides of residues 134–146 and 138–149 (References 24 and 25 respectively) of P25 also have been prepared. These peptides, which have several amino acids (138–146) in common, were both antigenically active in that each reacted with preparations containing specific anti-HBs activity, and they blocked antibody reactivity of sera of animals immunized with intact HBsAg. Linear peptides containing various overlapping amino acid residues in positions 138–158, covalently linked to carriers, have induced production of low levels of anti-HBs antibody in experimental animals (References 9b and 9c). The amino acid sequences of the immunogenic synthetic peptides according to the present invention reported in Table 2 as compared with the above studies have nothing in common. In fact, Reference 9c teaches that linear peptides 122–137 and 128–134 failed to elicit production of anti-HBs activity.

Whereas, the prior art (specifically, Reference 9a) teaches eliciting an antibody response to smaller peptides (e.g., having 14–15 residues), such response occurred only after repeated inoculation of covalently attached material to a carrier protein. In the present invention, antibody response to each of peptides 1 and 2 cyclized by disulfide bonds illustrated in FIGS. 2 and 3, respectively, occurs without using a carrier protein. It will be understood, however, that the incorporation of various adjuvant vehicles and/or protein carriers may increase the immunogenicity of the synthetic peptides according to the present invention.

The present invention, therefore, is well adapted to carry out the objects and attain the ends and advantages mentioned as well as others inherent therein. While a presently preferred embodiment of the invention has been given for the purpose of disclosure, numerous changes in compositions and steps of the methods will be readily apparent to those skilled in the art and which are emcompassed within the spirit of the invention and the scope of the appended claims.

What is claimed is:

1. A synthetic peptide for inducing an anti-hepatitis B virus response having the amino acid sequence of either amino acid residues 117-137 or 122-137 of the native P25 polypeptide of hepatitis B surface antigen and a disulfide bond between cysteine 124 and cysteine 137.

2. The composition of claim 1 wherein lysine is substituted for arginine 122.

3. The composition of claim 1 wherein serine is substituted for cysteine 121.

4. The composition of claim 1 having a B turn at residues 129-132.

5. The composition of claim 1 having a B turn at residues 135-137.

6. The composition of claim 1 further comprising an adjuvant vehicle.

7. A composition for inducing an anti-hepatitis B virus response comprising a synthetic peptide having the amino acid sequence:

(a)—thr—cys—met—thr—thr—ala—gln—
     123

—gly—thr—ser—met—tyr—pro—ser—cys
                                        137 wherein (a) can be lys or lys-ser-pro-gly-thr-ser, and having a disulfide bond between cys 124 and cys 137.

8. The composition of claim 6 having a B turn at amino acids 129-132.

9. The composition of claim 8 having a B turn at amino acids 135-137.

10. A method of inducing an anti-hepatitis B virus response comprising administering an immunogenic amount of a synthetic peptide having the amino acid sequence of either amino acid residues 117-137 or 122-137 of the native P25 polypeptide of hepatitis B surface antigen and a disulfide bond between cysteine 124 and cysteine 137 to an animal.

11. The method of claim 10 further comprising incorporating the synthetic peptide into an adjuvant vehicle.

12. The method of claim 10 further comprising aggregating the synthetic peptide into micelles.

* * * * *